United States Patent [19]

Larson

[11] 4,020,837
[45] May 3, 1977

[54] HOLLOW PIERCING TIP FOR VIAL STOPPERS

[75] Inventor: Roger R. Larson, Champaign, Ill.

[73] Assignee: Pharmaco, Inc. (Entire), Champaign, Ill.

[22] Filed: Nov. 4, 1975

[21] Appl. No.: 628,741

[52] U.S. Cl. .......................... 128/218 N; 128/272.3
[51] Int. Cl.² .......................................... A61M 5/32
[58] Field of Search ............ 128/2 B, 214.4, 218 N, 128/218 P, 215, 216, 221, 329, 339, 347, 348, DIG. 16, 272.3

[56] References Cited

UNITED STATES PATENTS

| 2,437,697 | 3/1948 | Kalom ........................ 128/221 X |
| 2,560,162 | 7/1951 | Ferguson ........................ 128/221 |
| 2,716,983 | 9/1955 | Windischman et al. ............ 128/221 |
| 2,864,365 | 12/1958 | Szmukler et al. .................. 128/221 |
| 3,067,742 | 12/1962 | Linke et al. ............... 128/218 N X |
| 3,308,822 | 3/1967 | De Luca ........................ 128/221 |
| 3,477,423 | 11/1969 | Griffith ............................ 128/2 B |
| 3,788,119 | 1/1974 | Arrigo .......................... 128/221 X |
| 3,788,320 | 1/1974 | Dye ............................ 128/214 Y |
| 3,867,937 | 2/1975 | Schwartz .................... 128/214.4 X |
| 3,893,445 | 7/1975 | Hofsess ........................ 128/221 X |

FOREIGN PATENTS OR APPLICATIONS

| 1,225,009 | 6/1960 | France ............................... 128/221 |

Primary Examiner—Edgar S. Burr
Assistant Examiner—Paul J. Hirsch
Attorney, Agent, or Firm—Clarence A. O'Brien; Harvey B. Jacobson

[57] ABSTRACT

An elongated cylindrical body is provided and includes a diametrically reduced sharpened tubular needle extension on one end for opposing and piercing the puncturable seal of a medicament vial. The other end of the cylindrical body includes a slightly inwardly tapering diametrically enlarged counterbore communicated at its inner end with the interior of the tubular needle extension. The body is provided for support from a safety cap secured over the conventional closure of a medicament vial provided with a puncturable seal with the needle structure guidingly supported from a central tubular mounting portion of the safety cap outwardly of the puncturable seal of the vial for movement of the sharpened tubular needle extension toward, in engagement with and through the puncturable seal, whereby the conical tip of a syringe to have medicament introduced thereinto from the medicament vial may be seated within the inwardly tapering counterbore in fluid-tight sealed engagement therewith and the needle structure may be used to transfer medicament from within the vial into the syringe. The sharpened terminal end of the tubular needle extension is of a configuration other than the usual planar bevel to ensure the ability of the sharpened terminal end of the needle extension to retain its shape under axial pressure upon its engagement with the puncturable seal of a medicament vial, even when the needle structure is constructed of inexpensive plastic for manufacture by means of relatively inexpensive high volume molding manufacturing processes.

6 Claims, 5 Drawing Figures

HOLLOW PIERCING TIP FOR VIAL STOPPERS

The needle structure of the instant invention comprises an improvement over the corresponding needle structure disclosed in my copending U.S. application Ser. No. 467,802, filed May 7, 1974, now U.S. Pat. No. 3,940,003, dated Feb. 24, 1976, the supportive safety cap structure of my above-mentioned prior application for a Seal Piercing Needle Structure being incorporated herein by this reference thereto.

BACKGROUND OF THE INVENTION

The safety cap of my above-noted prior patent supports a tubular needle structure for advancement toward, engagement with and movement through the puncturable seal of an associated unit dose medicament vial. The needle construction of the instant invention comprises an improvement over the needle structure disclosed in my prior patent in that conventionally beveled piercing tips of hollow needles constructed of plastic tend to bend upon their engagement with conventional medicament vial puncturable seals and axial thrust upon the needle structure to force the beveled tip through the seal. This bending is a result of the thin plastic wall portion of the sharpened needle tip and is always present. However, certain puncturable seals are tougher than others and an individual seal may have an unusually tough central area thereof to be pierced. Under these circumstances, a seal piercing needle structure constructed of plastic bends sufficiently to impede penetration of the sharpened end of the needle structure through the seal to the extent that the center section of the seal engaged by the needle structure sufficiently resists penetration by the needle structure to be excessively inwardly displaced to the extent that all inward movement of the needle structure to the seal piercing position is insufficient to cause the sharpened tip of the needle structure to complete the seal piercing operation. Of course, if time is a factor in administering the medication and the puncturable seal of the medicament vial from which the medication is to be drawn resists penetration by the associated needle structure serious consequences may result.

BRIEF DESCRIPTION OF THE INVENTION

The needle structure of the instant invention is of a conventional shape insofar as the supportive portions thereof are concerned and the improvement of the invention resides solely in the configuration of the sharpened tip of the needle structure. The sharpened tip is beveled, but the two beveled surfaces of the tip are arranged in stepped beveled areas defining inner and outer annular zones extending substantially fully about and concentric with the center passage formed through the needle, the inner and outer beveled zones being joined at corresponding points about their peripheries by means of a reasonably blunt radially extending area providing sufficient wall strength at the extreme tip of the sharpened point to resist deflection of the sharpened point of the needle construction upon contact with and its being forced through the puncturable seal of a medicament vial.

The main object of this invention is to provide a tubular needle structure of the type above described having sufficient wall thickness and strength at its sharpened tip to effectively resist bending upon engagement with and being forced through the puncturable seal of a medicament vial, even when the needle structure is constructed of plastic by injection molding processes.

Another object of this invention is to provide a tubular needle structure including an ordinary lumen opening therein as opposed to other forms of needle structures such as the "spiked" form wherein an imperforate conical tip is provided and side openings opening into the interior of the needle are provided at a point spaced from the conical tip thereof, this form of needle structure being considerably more expensive to produce by molding processes than a more or less conventional lumen opening equipped needle structure utilizing a core pin in the molding process which pulls through the cannula when the needle structure is injection molded.

Another important object of this invention is to provide a needle structure which will effectively resist "plugging" of the seal punctured thereby and which will therefore substantially eliminate the possibility of a plug of the core being drawn into the associated syringe, even when a filter within the needle structure is not provided.

A final object of this invention to be specifically enumerated herein is to provide a hollow needle structure in accordance with the preceding objects and which will conform to conventional forms of manufacture, be of simple construction and easy to use so as to provide a device that will be economically feasible and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
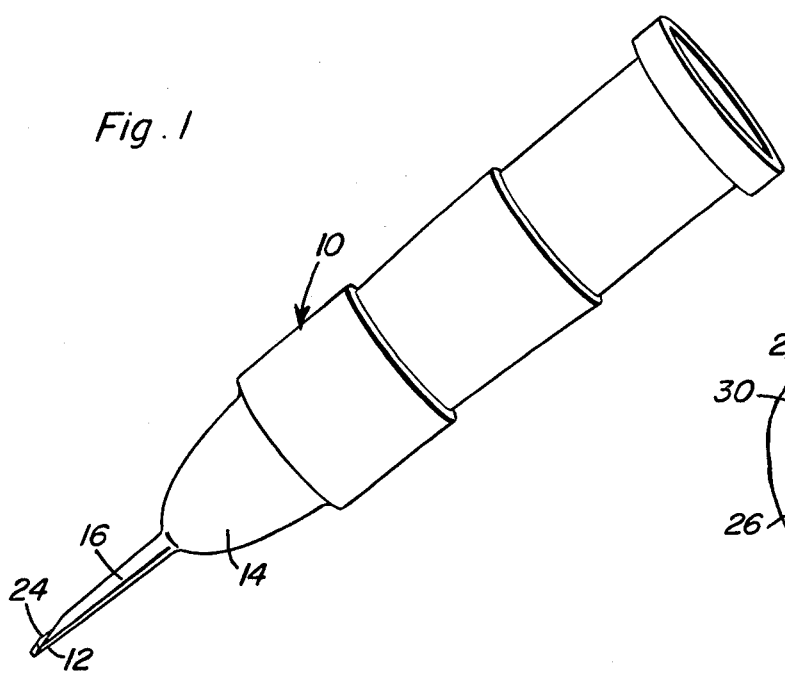
FIG. 1 is a perspective view of the tubular needle structure of the instant invention.
Figure 2:
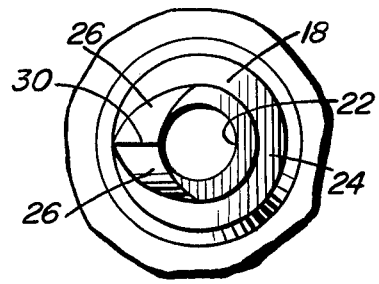
FIG. 2 is an enlarged fragmentary and elevational view of the needle structure as seen from the sharpened tip end thereof.

Referring now more specifically to the drawings, the numeral 10 generally designates the needle structure of the instant invention. The needle structure 10 is substantially identical to the corresponding needle structure designated by the reference numeral 34 in my prior U.S. Pat. No. 3,940,003 except for the sharpened tip end 12 of the needle structure 10 and the provision of a bulbous portion 14 defined by the needle structure 10 at the base end of the needle extension 16 of the needle structure 10. With attention now invited more specifically to FIGS. 2, 3, 4 and 5 of the drawings it may be seen that the sharpened tip end 12 includes an outer partially annular bevel 18 and an inner partial annular bevel 20 with the bevel areas 18 and 20 substantially concentric relative to each other and the center cylindrical passage or bore 22 formed through the extension 16. From FIGS. 3, 4 and 5 of the drawings it may be seen that a reduced wall thickness portion 24 of the extension 16 joins the bevel areas 18 and 20, but that the walls of the portion 24 are beveled as at 26 on opposite sides of a blunt edge 30 defined at the intersection of the beveled areas 26. The blunt edge 30 interconnects and extends between the outer and inner beveled areas 18 and 20 at the extreme tip of the sharpened tip end 12. The edge 30 extends generally along a radius of the center bore 22 and the beveled areas 26 extend along lines angularly displaced approximately 60 degrees relative to each other.

Figure 3:
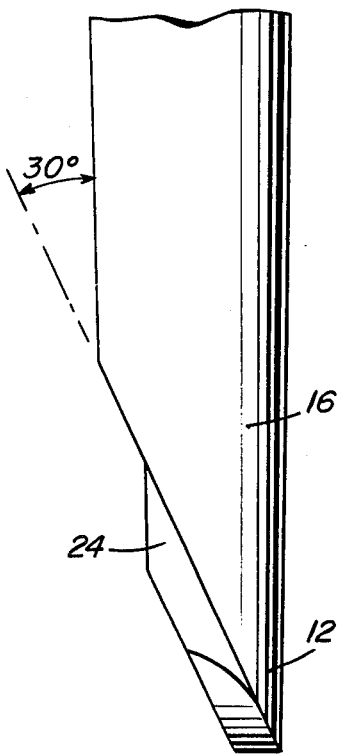
FIG. 3 is an enlarged fragmentary side elevational view of the left side of the sharpened tip of the needle structure.
Figure 4:
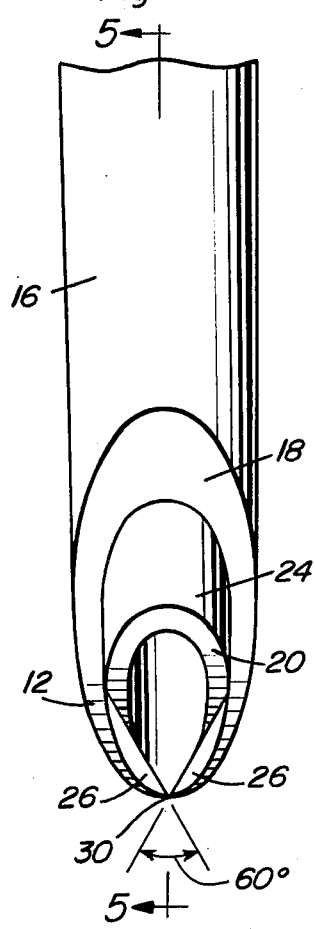
FIG. 4 is a fragmentary enlarged front elevational view of the sharpened tip of the needle structure.
Figure 5:
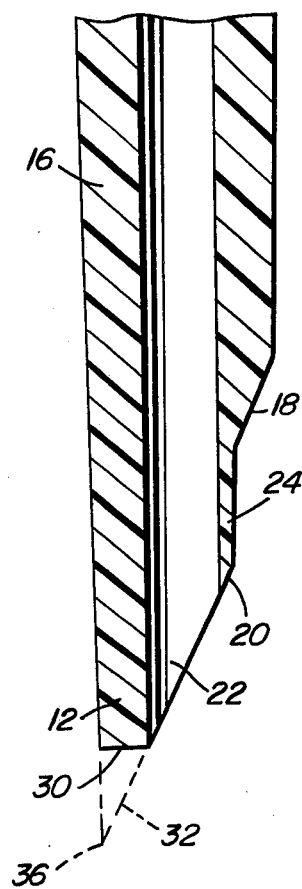
FIG. 5 is a longitudinal sectional view taken substantially upon the plane indicated by the section line 5—5 of FIG. 4.

It will be noted from FIGS. 4 and 5 of the drawings that the portion 24 defines an appreciably reduced wall thickness area of the needle extension 16. However, this area is so short as measured in an axial direction and includes such a small radius of curvature so as to resist excessive deflection when forced into contact by the puncturable seal of a medicament vial. Further, the portion 24 is disposed to the rear of the edge 30 which first contacts and initially punctures the seal of a medicament vial and accordingly, the portion 24 is never subject to bending forces of the magnitude resisted by the bevel edge 30. Of course, from FIGS. 3 and 5 of the drawings it may be seen that the bevel edge 30 is of longitudinal extent equal to the full thickness of the walls of the needle extension 16. Further, if the bevel area 20 illustrated in FIG. 5 was continued downwardly to the left so as to extend to the extreme left-hand outer surface of the needle extension 16 as illustrated in phantom lines 32 the apex portion 36 would constitute such a thin point as to be readily deflected upon its engagement with a puncturable seal of a medicament vial. When this deflection becomes excessive either due to an unusually resistant medicament vial seal or perhaps a weakened tip area full piercing of the medicament vial seal as a result of normal axial displacement of the needle structure 10 to advance the latter through the seal does not occur due to the center portion of the seal contacted by the needle structure being excessively inwardly displaced relative to the associated medicament vial.

However, it may be appreciated upon comparing the bevel edge 30 and the conventional bevel edge 32 that the bevel edge 30 is of considerably greater thickness at its point of initial contact with the puncturable seal and is in fact not beveled to only one side but to both sides as at 26 thereby evenly distributing the lateral forces exerted on the puncturable seal by the edge 30 to eliminate deflection of the extreme tip end of the needle extension 16. Consequently, the bevel edge 30 more readily penetrates the seal being punctured and thus reduces the force requirements to complete the axial thrust of the needle extension 16 through the seal to be punctured.

Although the needle extension 16 might be provided only with the bevel area 20 and the outer walls of the extension 16 extending the full length thereof to the bevel area 20, with the needle still being provided with the bevel areas 26 defining the bevel edge 30, by providing the bevel area 18 behind the bevel area 20 initial contact of the needle extension 16 with the area of the seal to be punctured is effected by the relatively thin walled portion 24 connecting the bevel areas 18 and 20 and the effectiveness of the initial cut through the seal by the bevel edge 30 and the bevel areas 26 is continued through a greater extent of the axial movement of the extension 16 through the seal with that portion of the bevel area 18 disposed at the left side of FIG. 3 being forced through the seal being punctured only after at least three-quarters of the total front area of the extension 16 outwardly of the central bore 22 formed therethrough has already substantially fully penetrated the seal. For this reason, the needle extension 16 operates to more easily initially begin penetration of the seal to be punctured by the edge 30 and prolongs the puncturing process of the seal throughout a greater amount of axial displacement of the needle extension 16 relative to the seal being punctured.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A needle structure for piercing the resilient stopper of a medicament vial or the like, said structure including an elongated tubular body constructed of stiff, but bendable plastic having a first large diameter supportive end and a second diametrically reduced needle extension defining end, said second end including a central longitudinal small diameter bore extending therethrough, the free end of said second end including at least one beveled end face through which said bore opens and which extends continuously about said bore on opposite sides of a narrow radial zone of said extension at the outermost extremity of said beveled end face extending between the outer surface of the corresponding peripheral portion of said extension and the adjacent peripheral portion of said bore, said radial zone being defined by a blunt radial ridge having its apex facing outwardly of said free end and formed between oppositely beveled surfaces of said extension extending between said outermost extremity of said beveled end face and the adjacent outer side surface of said extension.

2. The combination of claim 1 wherein said beveled end face is inclined generally 30° relative to the longitudinal centerline of said bore.

3. The combination of claim 1 wherein said oppositely beveled surfaces define an included angle of generally 60°.

4. A needle structure for piercing the resilient stopper of a medicament vial or the like, said structure including an elongated tubular body having a first large diameter supportive end and a second diametrically reduced needle extension defining end, said second end including a central longitudinal small diameter bore extending therethrough, the free end of said second end including at least one beveled end face through which said bore opens and which extends about said bore on opposite sides of a radial zone of said extension at the outermost extremity of said beveled end face extending between the outer surface of the corresponding peripheral portion of said extension and the adjacent peripheral portion of said bore, said radial zone being defined by a blunt radial ridge having its apex facing outwardly of said free end and formed between oppositely beveled surfaces of said extension extending between said outermost extremity of said beveled end face and the adjacent outer side surface of said extension, said beveled end face extending throughout a partial annular zone immediately outwardly of and coaxial with said bore, but being spaced inwardly from the outer surfaces of said extension, said extension including a second beleved end face disposed outwardly of and coaxial with the first mentioned beveled end face and substantially paralleling the latter, the plane of said second beveled end face being spaced slightly along said extension from the plane of the first mentioned beveled end face toward the first end of said needle structure, said beveled surfaces extending between corresponding portions of said beveled end faces and the first mentioned beveled end face being carried by a generally cylindrical projection of said body extending outwardly of said second beveled end face generally coaxial with said bore.

5. The combination of claim 4 wherein said beveled end face is inclined generally 30° relative to the longitudinal centerline of said bore.

6. The combination of claim 5 wherein said oppositely beveled surfaces define an included angle of generally 60°.

* * * * *